(12) United States Patent
Nicoletti

(10) Patent No.: US 9,518,909 B2
(45) Date of Patent: *Dec. 13, 2016

(54) PARTICLE DETECTOR AND METHOD FOR PRODUCING SUCH A DETECTOR

(71) Applicant: Commissariat A l'Energie Atomique Et Aux Energies Alternatives, Paris (FR)

(72) Inventor: Sergio Nicoletti, Sinard (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/496,072

(22) Filed: Sep. 25, 2014

(65) Prior Publication Data

US 2015/0116710 A1    Apr. 30, 2015

Related U.S. Application Data

(63) Continuation of application No. 13/811,499, filed as application No. PCT/IB2011/053213 on Jul. 19, 2011, now Pat. No. 8,867,035.

(30) Foreign Application Priority Data

Jul. 22, 2010    (FR) ...................................... 10 03081

(51) Int. Cl.
  *G01N 21/00*    (2006.01)
  *G01N 15/02*    (2006.01)
  (Continued)

(52) U.S. Cl.
  CPC ........... *G01N 15/0211* (2013.01); *G01N 15/06* (2013.01); *G01N 15/1484* (2013.01);
  (Continued)

(58) Field of Classification Search
  CPC  G01N 21/53; G01N 15/0205; G01N 15/1459; G01N 21/51; G01N 15/1434
  (Continued)

(56) References Cited

U.S. PATENT DOCUMENTS 6,448,777 B1 *  9/2002  Abdel-Rahman et al. ... 324/464
6,618,144 B1 *  9/2003  Reed ............................. 356/343
  (Continued)

FOREIGN PATENT DOCUMENTS

CN    10 037 8836 C    8/2005
DE    42 30 087 A1    3/1994
WO    WO 97/12223 A1    4/1997

OTHER PUBLICATIONS

International Search Report and Written Opinion for Appliation No. PCT/IB2011/053213 dated Nov. 9, 2011.
  (Continued)

*Primary Examiner* — Tarifur Chowdhury
*Assistant Examiner* — Md M Rahman
(74) *Attorney, Agent, or Firm* — Alston & Bird LLP

(57) ABSTRACT

The invention relates to a particle detector including a substrate made of a semiconductor material, in which at least one through-cavity is formed, defined by an input section and an output section, wherein the input section thereof is to be connected to an airflow source, the substrate supporting: an optical means including at least one laser source, and at least one waveguide connected to the at least one laser source and leading into the vicinity of the output section of the cavity; and a photodetector located near the output section of the cavity and offset relative to the optical axis of the optical means.

20 Claims, 2 Drawing Sheets

(51) Int. Cl.
*G01N 15/14* (2006.01)
*G01N 21/53* (2006.01)
*G01N 15/06* (2006.01)
*G01N 15/00* (2006.01)
*G01N 21/47* (2006.01)

(52) U.S. Cl.
CPC ............ *G01N 21/53* (2013.01); *G01N 21/532* (2013.01); *G01N 2015/0038* (2013.01); *G01N 2021/4726* (2013.01); *G01N 2201/06113* (2013.01); *G01N 2201/0873* (2013.01)

(58) Field of Classification Search
USPC ......................................................... 356/338
See application file for complete search history.

(56) References Cited

U.S. PATENT DOCUMENTS

| | | | | |
|---|---|---|---|---|
| 6,693,708 | B1* | 2/2004 | Hunter | 356/237.5 |
| 7,015,355 | B2 | 3/2006 | Zeyss et al. | |
| 2002/0016068 | A1* | 2/2002 | Nakano et al. | 438/689 |
| 2002/0160363 | A1* | 10/2002 | McDevitt | C12Q 1/37 435/6.12 |
| 2006/0096075 | A1 | 5/2006 | Robinson et al. | |
| 2007/0099315 | A1* | 5/2007 | Maa et al. | 438/22 |
| 2008/0186489 | A1* | 8/2008 | Ahn | G01N 15/065 356/337 |
| 2009/0003761 | A1 | 1/2009 | Matsuoka et al. | |
| 2009/0115603 | A1* | 5/2009 | Tabe | 340/540 |
| 2011/0294139 | A1 | 12/2011 | Takeda | |

OTHER PUBLICATIONS

Hazart, J. et al., *Robust sub-50-nm CD Control by a Fast-Goniometric Scatterometty Technique*, Proc. SPIE, vol. 6518, 65183A (2007).

Lopez-Tejeira, F. et al., *Efficient Unidirectional Nanoslit Couplers for Surface Plasmons*, Nature Physics, vol. 3 (May 2007).

Moreno, M. et al., *Photosensor and Optical Waveguide Coupling in Silicon Technology*, Sensors and Actuators A62 (1997).

Romeo, P. R. et al., *Heterogeneous Integration of Electrically Driven Microdisk Based Laser Sources for Optical Interconnects and Photonic ICs*, Optics Express 3864, vol. 14, No. 9 (May 1, 2006).

Rouviere, M. et al., *Ultrahigh speed Germaniun-on-Silicon-on-Insulator Photodetectors for 1.31 and 1.55 μm Operation*, Applied Physics Letters 86, 231109 (2005).

Stutius, W. et al., *Silicon Nitride Films on Silicon for Optical Waveguides*, Applied Optics, vol. 15, No. 12 (Dec. 1977).

Trinh, P. D. et al., *Silicon-on Insulator (SOI) Phase-Array Wavelength Multi/Demultiplexer With Extremely Low-Polarization Sensitivity*, IEEE Photonics Technology Letters, vol. 9, No. 7 (Jul. 1997).

Wang, X. et al., *A Novel Optical Instrtument for Estimating Size Segregated Aerosol Mass Concentration in Real Time*, Aerosol Science and Technology (Sep. 1, 2009).

* cited by examiner

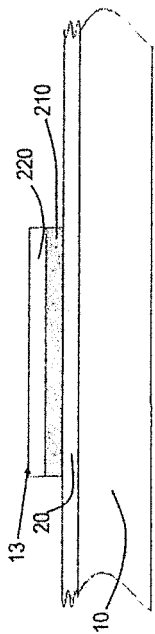
FIGURE 4d
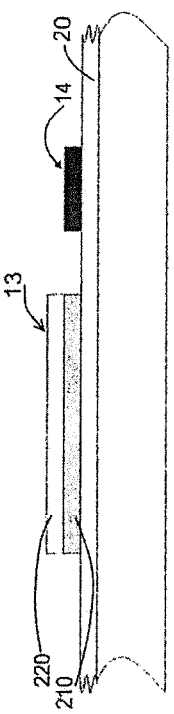
FIGURE 4e
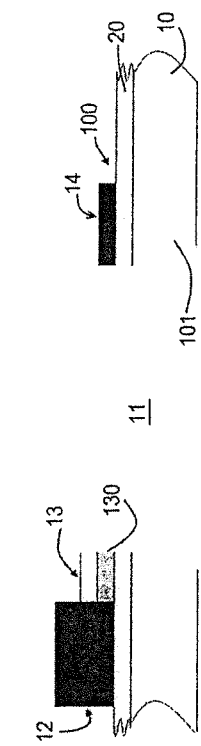
FIGURE 4f
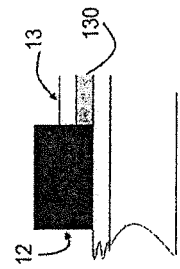
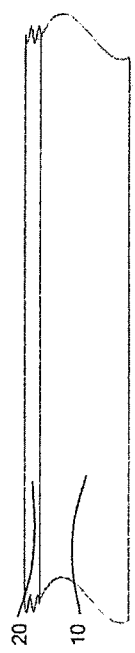
FIGURE 4a
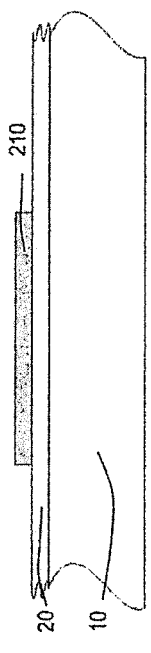
FIGURE 4b
FIGURE 4c

PARTICLE DETECTOR AND METHOD FOR PRODUCING SUCH A DETECTOR

CROSS REFERENCE TO RELATED APPLICATIONS

This application is a continuation of U.S. application Ser. No. 13/811,499, filed Jan. 22, 2013, which is a national stage application filed under 35 USC 371 of International Application No. PCT/IB2011/053213, filed Jul. 19, 2011, which claims priority from FR patent application 10 03081 filed Jul. 22, 2010, the entire contents of which are incorporated herein by reference.

FIELD

The invention relates to the field of the detection of particles, in particular particles present in the atmosphere.

BACKGROUND

Their size may vary between a few nanometers for the droplets present in clouds, and a few tens of microns for the dust particles generated by human activities or by natural effects.

The effects of these particles on human health are becoming an increasing concern.

They depend essentially on the capacity of these particles to be absorbed by the respiratory tracts.

The particles which have a large size remain trapped in the nasopharyngeal cavity, while the particles with a smaller size are capable of penetrating into the alveolar section of the lungs.

Likewise, the fraction of particles exhaled gradually increases with the dimension of these particles.

Consequently, the particles which have the smallest size are considered to be those most dangerous for human health.

This is why monitoring the level of human exposure to the particles is an important element in evaluation of the health risks at the place of work and in the outside environment.

This monitoring requires simultaneous measurement of the concentration and the size of the particles present in the ambient air for at least one given particle size.

Thus, the national and European standards currently in force require monitoring of the PM10 parameter, that is to say the number of particles per unit volume which are present in the atmosphere and have a dimension greater than 10 µm. Other parameters may also be envisioned, such as PM2.5 or PM1, that is to say the number of particles per unit volume having a dimension greater than 2.5 µm or 1 µm.

In the prior art, there are three known techniques used for measuring the concentration of particles in the atmosphere: gravimetric measurement, the β technique and the technique of optical absorption and diffraction.

Gravimetric measurement consists in filtering the ambient air with the aid of a gravimetric filter having controlled porosity. This filter collects all the particles below a given size, referred to as the cutoff size.

It is generally associated with a second filter having selective admission, which removes the particles which have a large size, and with a pump which ensures a constant air flow throughout the system.

In order to determine the quantity of particles, the filter is subsequently weighed.

Thus, in order to obtain information about the size of the particles, it is expedient to use a plurality of different filters.

This technique requires the use of numerous consumables and the conduct of a large number of operations. This is why it is relatively time-consuming and expensive to implement.

Lastly, this technique only makes it possible to deliver an average measurement and cannot provide any information about the distribution of the particles as a function of time.

The β technique uses a low-energy carbon-14 source which provides a constant flux of β electrons that are detected by a Geiger tube or by a matrix of photodiodes.

A band filter is interposed between the source and the detector.

The particle measurement cycle starts with calibration.

A gas sample is subsequently sent through the band filter, on which all the particles whose size is greater than a given size, for example 10 µm, are collected.

The filter is subsequently interposed again between the source and the detector, and the transmission of the β electrons is measured.

The difference in β electron transmission through the filter is directly proportional to the mass of particles accumulated on the filter.

Like the gravimetric technique, this β technique uses a fairly large quantity of consumables. Furthermore, it only makes it possible to provide an average measurement, and it therefore does not provide any information about the distribution of the particles as a function of time.

It may also be noted that information about the size of the particles requires the use of a plurality of filters.

Lastly, the β technique requires the presence of a radiation source and a system capable of managing complex operations.

The technique of optical absorption and diffraction is based on measurement of the amount of light diffracted by the particles present in the working volume of a detector.

Mention may thus be made of a photometric detector which measures the amount of light scattered by the interaction with the particles.

Such a detector makes it possible to cover a fairly wide range of particle concentrations.

However, the signal which it delivers is proportional to the size, the shape and the optical properties of the particles, and cannot provide an estimate of the average size of the particles.

Furthermore, the estimate of the concentration depends on the difference between the amount of light absorbed and the amount of light transmitted. For this reason, the difference becomes very small when the particle concentration decreases and it is no longer possible to make a correct estimate.

Document DE-4230087 describes another type of particle detector which comprises a substrate, with an etched groove and an integrated waveguide, as well as a light source and a light receiver which are independent of the substrate. The waveguide is interrupted by the etched groove which allows passage of the medium to be analyzed. Furthermore, a membrane provided with holes is provided in order to determine the minimum size of the particles to be measured, and in order to filter the flowing medium.

Thus, with this detector the particles are prefiltered and their passage between the two parts of the waveguide subsequently leads to dissipation of the light. The difference in light flux passing through the two parts is detected and related to the number of particles passing through the groove.

Such a detector is relatively complex, because it requires prefiltering. Furthermore, the use of discrete components conventionally entails adjustment problems.

Mention may also be made of the optical particle counter, which uses a laser source focused in proximity to an air jet containing the particles to be detected. The lighted diffracted, scattered or reflected by the particles is collected by a photodiode, which is off-center with respect to the optical axis.

Such an optical particle counter is described in particular in the article "A novel optical instrument for estimating size segregated aerosol mass concentration in real time" by X. Wang et al. (Aerosol science and technology, 1 Sep. 2009).

An optical particle counter has the benefit of delivering the number of particles and an estimate of their size in real time, owing to the measurement of the intensity of the light collected.

However, the quality of the measurements is contingent on precise positioning of the laser beam and of the air jet.

One major drawback of such an optical counter is the risk of underestimating the concentration of particles. This may be due to the simultaneous presence of a plurality of particles in the detection volume, these particles being partially or completely superimposed in relation to the laser beam.

Furthermore, an optical counter conventionally consists of discrete components, which raises problems of bulk, alignment and adjustment.

Thus, document WO97/12 223 describes a flow cytometer comprising two components: an optical head and a disposable flow module. The optical head comprises a laser and two photodetectors. The flow module consists of a substrate etched with a channel for the passage of a flow.

This document indicates that the optical components may be mounted in a rigid housing in order to preserve their alignment. However, these are discrete components which are furthermore independent of the module, since the latter is a disposable element.

In all cases, devices consisting of discrete elements also lead to significant manufacturing costs.

SUMMARY

It is an object of the invention to overcome the drawbacks of the known techniques by providing a device for detecting particles which has the advantages of the optical particle counters, that is to say the possibility of measuring both the concentration and the size of the particles in real time, but which are compact, having perfectly controlled dimensions, with a reduced manufacturing cost and having robustness greater than that of simple mechanical mounting.

Furthermore, the method used to obtain this device makes it possible to produce a plurality of components simultaneously and without additional cost, which makes it possible to reduce the risks of underestimating the number of particles.

Lastly, this device can operate in a large range of wavelengths, which makes it possible on the one hand to detect particles whose size is much less than one micron and, on the other hand, to acquire information relating to the chemical nature of the particles.

Thus, the invention relates to a particle detector comprising a substrate in which at least one through-cavity, delimited by an entry cross section and an exit cross section, is formed, its entry cross section being intended to be connected to a source of an air flow, said substrate supporting:

optical means comprising at least one laser source and at least one waveguide, which is connected to said at least one laser source and opens in proximity to the exit cross section of said cavity, thereby ensuring the emission of a light beam, and photodetector means located in proximity to the exit cross section of said cavity and offset with respect to the optical axis, in order to detect the scattered light.

Preferably, the optical means and the photodetector means are located on the same face of the substrate.

Advantageously, said at least one cavity has a variable cross section which decreases from the entry cross section to the exit cross section.

Advantageously, the optical means also comprise at least one photonic device, at the opposite end of the waveguide from the laser source, for focusing the light in said at least one cavity.

Furthermore, the laser source and the waveguide may be connected by means of a coupler or by evanescent coupling.

In a first embodiment, the detector means comprise a plurality of photodetectors associated with a through-cavity.

In another embodiment, the substrate comprises a plurality of through-cavities.

The invention also relates to a method for producing a particle detector according to the invention, comprising the following steps:

(a) depositing a first layer of a material having a first optical index $n_1$ on a substrate, (b) depositing a second layer of a material having a second optical index $n_2$ on this first layer, $n_2$ being greater than $n_1$, (c) producing at least one waveguide by structuring the second layer, then by depositing and structuring a third layer of a material having a third optical index $n_3$, $n_3$ being less than $n_2$, (d) producing at least one photodetector, (e) producing at least one laser source at one end of said at least one waveguide, (f) producing electrical interconnections between the various elements produced on the substrate, and (g) by etching in the substrate, producing at least one through-cavity opening in proximity to the opposite end of said at least one waveguide from the laser source and in proximity to said at least one photodetector, the photodetector being offset with respect to the optical axis.

Preferably, steps (a) to (f) are carried out on the same face of the substrate.

Advantageously, the substrate consists of a semiconductor material, in particular silicon.

Furthermore, the thickness of the first and second layers deposited on the substrate corresponds substantially to the wavelength of the laser source.

Preferably, the structuring of the second layer and of the third layer, which is provided in step (c), comprises a lithography step and an etching step.

During step (d), the photodetector produced is a photodiode obtained by producing a pn junction on the substrate.

Furthermore, step (e) is advantageously carried out by hybridization or by heterogeneous integration.

Lastly, after step (c), the method according to the invention may comprise an additional step consisting in nanostructuring the opposite end of the waveguide from the laser source, in order to produce a focusing function.

BRIEF DESCRIPTION OF THE DRAWINGS

The invention will be better understood and other objects, advantages and characteristics thereof will become clearer on reading the following description, which is given with reference to the appended drawings, in which:

FIGS. 4a to 4f represent steps of a method for producing the particle detector illustrated in FIG. 1.

DETAILED DESCRIPTION

The elements common to the various figures are denoted by the same references.

Figure 1:
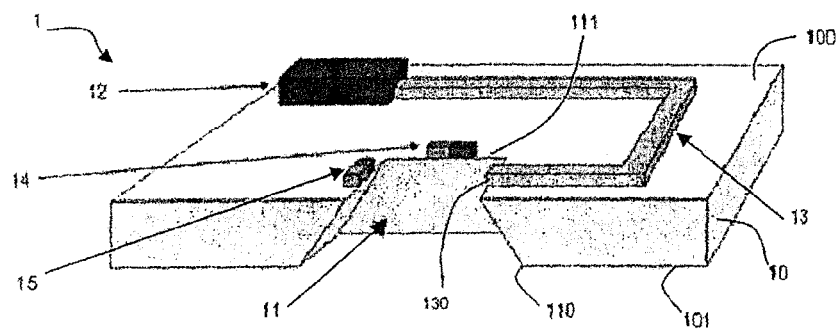
FIG. 1 is a perspective view of a first exemplary embodiment of a particle detector according to the invention.

The particle detector 1 illustrated in FIG. 1 comprises a substrate 10, in particular consisting of silicon.

In general, this substrate must be compatible with the conventional techniques of micro- and nanofabrication of miniaturized components. It may thus be produced from a semiconductor material, such as Si or GaAs, or alternatively from glass or sapphire.

Furthermore, it is preferably produced from a rigid material.

A through-cavity 11 is formed in this substrate 10. This cavity 11 is intended to receive and direct an air flow from the entry cross section 110 to the exit cross section 111.

Preferably, the cross section of the cavity 11 decreases between the entry cross section 110 and the exit cross section 111, so as to guide the air flow better.

This cavity 11 may be obtained by etching, and in particular by anisotropic etching.

During operation, the entry cross section 110 is connected to an air flow comprising the particles to be detected.

The substrate 10 has a substantially planar shape, or at least a planar surface such as the face 100. On its face 100 on which the exit cross section 111 of the cavity is defined, it also comprises a laser source 12.

This laser source is directly integrated on the substrate 10, for example according to a method of co-integration by hybridization or heterogeneous integration.

The article "*Heterogeneous integration of electrically driven microdisk based laser sources for optical interconnects and photonic ICs*" by P. Rojo Romeo et al. (Optics Express 3864-1 May 2006/vol. 14, No. 9) may thus be cited.

On the face 100, the device 1 also comprises a waveguide 13 which connects the laser source 12 to the cavity 11. The laser source 12 and the waveguide 13 constitute the optical means of the particle detector 1.

During operation, the light radiation generated by the laser source 12 is injected into the waveguide 13 with the aid of a coupler or by evanescent coupling.

It is emitted by the waveguide in a given direction, referred to as the optical axis of the optical means.

Thus, the light radiation generated by the laser source 12 is directed toward the exit cross section 111 of the cavity, the latter constituting the space of interaction between the particles and the light radiation.

The width and thickness of the waveguide 13 may vary between a few hundreds of nanometers and a few micrometers. In general, the dimensions of the waveguide are selected as a function of the wavelength range of the laser source.

This waveguide may be obtained according to different methods known in the prior art, in a wide range of wavelengths.

The article "*Silicon nitride films on silicon for optical waveguides*" by W. Stutius and W. Streifer (Applied optics/vol. 16, No. 12/December 1977) or the article "*Photosensor and optical waveguide coupling in silicon technology*" by M. Moreno et al. (Sensors and Actuators—A62 (1997)) may thus be cited.

Furthermore, the opposite end 130 of the waveguide 13 from the laser source 12 may comprise a photonic device in order to produce a focusing function.

This photonic device may be obtained by nanostructuring. For example, it makes it possible to increase the density and/or sensitivity of the light emitted by the waveguide.

The article "*Efficient unidirectional nanoslit couplers for surface plasmons*" by F. López-Tejeira et al. (Nature physics/vol. 3/May 2007) may thus be cited.

On the face 100 of the substrate 10, a photodetector 14 is also provided in proximity to the cavity 11 and therefore to the entry cross section 111.

The photodetector 14 is offset with respect to the optical axis or not aligned with this optical axis.

This photodetector 14 may in particular consist of a pyrometer or a bolometer. It advantageously consists of a photodiode comprising a pn junction.

Photodiodes have the advantage of being more sensitive and of being simpler to produce.

When the particle detection device operates with wavelengths lying in the visible or near infrared range, the photodiode may consist of a pn junction produced from silicon. For wavelengths lying beyond 1.1 µm, the photodiode may be produced by a pn junction of composite semiconductor or germanium.

It has been indicated that the end 130 of the waveguide and the photodetector are located in proximity to the cavity. This means that they are close enough to the cavity in order to fulfill their respective functions: emission of a light beam into the cavity and detection of the scattered light.

Furthermore, the photodetector need not be located on the same axis as the light beam emitted by the waveguide, in order to fulfill its detection function.

The device 1 may comprise a photodiode 15 substantially opposite the end 130 of the waveguide, the photodiode 15 and the end 130 being separated by the cavity 11. The function of this photodiode is to measure the power of the laser.

Thus, the particle detector according to the invention comprises three main units: the optical means, a space of interaction between a particle flow and the light radiation, and photodetector means.

Preferably, the optical means and the photodetector means are located on the same face of the substrate. This facilitates manufacture of the detector, as can be seen from FIGS. 4a to 4f.

Its operation is substantially similar to that of a conventional optical particle counter.

However, the first advantage which this particle detector presents, compared with conventional optical particle counters, is due to the fact that all of its components are produced on the same substrate by using manufacturing methods derived from CMOS and/or MEMS technologies.

Moreover, these methods conventionally ensure a degree of dimensional control, a structural rigidity and a robustness which are far superior to those obtained with simple mechanical mounting, such as that of conventional optical particle counters. The problems of alignment or adjustment, which arise in detectors formed by discrete components, are thus resolved.

In the same train of thought, the particle detector according to the invention can be miniaturized, all its constituent means being produced on the same chip.

In particular, if the substrate is produced from a semiconductor material, all the means necessary for the particle detector to function, in particular the preamplifiers associated with the photodetectors, may be produced on the substrate. It is therefore not necessary to produce an electronics board independent from the substrate.

The detector obtained is therefore fully portable and autonomous, which cannot easily be achieved when the detector is obtained by assembling discrete components.

Another advantage of the particle detector according to the invention is due to the fact that its various components are produced simultaneously on the same substrate.

It is therefore conceivable to produce particle detectors according to the invention which comprise a plurality of laser sources and/or photodetector means, without altering their manufacturing cost.

By virtue of this multiplication of optical means and photodetectors, the risk of underestimating the particle concentration can be reduced considerably, which risk is high with conventional optical particle counters.

Furthermore, this multiplication of the optical means and photodetector means allows precise estimation of the size of the particles by scatterometry methods.

This emerges in particular from the article "*Robust sub-50-nm CD control by a fast-goniometric scatterometry technique*" by J. Hazart et al. (Proc. SPIE, Vol. 6518, 65183A (2007)). The latter shows that the signal detected by a plurality of photodetectors has been used in order to determine the shape and the dimensions of objects scattering light.

Thus, the manufacturing methods used allow a better guarantee of the alignment of the various components of the particle detector than in the case of simple assembly of discrete components.

Likewise, the fact that all the components are integral with the substrate makes them less subject to vibrations and fluctuations in temperature. In particular, the temperature of the detector may be stabilized by a Peltier device. This makes the particle detector more stable and the measurements reproducible.

Another advantage of the particle detector according to the invention resides in the fact that it makes it possible to detect particles whose size is substantially less than one micron.

In fact, by virtue of the production method employed, the wavelength range available at the laser source is between about 1.5 µm and about 450 nm.

For this reason, the detector can make it possible to analyze particles whose size is of the order of 0.5 µm or greater than 0.5 µm.

The particle detector according to the invention therefore satisfies the current standards and will therefore be useable with more stringent future standards.

Furthermore, a particle detector according to the invention may include a plurality of laser probes and therefore generate a plurality of light beams.

In general, when there is a particle flowing through the cavity 11, a part of the light emitted by the waveguide 13 is diffracted, typically in all directions.

The photodetector 14 can thus measure a light flux which is a function of the intensity of the light beam emitted by the waveguide, the wavelength of the radiation, and the size and nature of the particle.

The photodetectors are advantageously placed in proximity to the cavity 11, which makes it possible to collect more photons and contributes to the precision of the measurement.

A method for producing a particle detector, such as the one illustrated in FIG. 1, will now be described with reference to FIGS. 4a to 4f.

In a first step (a) illustrated in FIG. 4a, a first layer 20 of a material having a first optical index $n_1$ is deposited on a face of a substrate 10.

This substrate 10 may advantageously be silicon. In practice, all substrates compatible with the conventional technologies of micro- and nanofabrication may be used.

When the detector is required to integrate a laser source generating light radiation in the infrared range, the substrate may be the first Si layer of an SOI stack (Silicon on Insulator).

The material used for producing the first layer 20 is typically $SiO_2$.

Its thickness is of the order of the wavelength used for the detector. It is therefore, for example, between 0.1 and 1.5 µm.

In a second step (b) illustrated in FIG. 4b, a second layer 21 of a material having a second optical index $n_2$ is deposited on the first layer 20. The second optical index $n_2$ is greater than the first index $n_1$.

The material used to produce the second layer 21 is typically $Si_3N_4$, $Al_2O_3$ or $HfO_2$ when the optical detector is intended to integrate a laser source generating light radiation in the visible range. This material may be Si for a laser source generating light radiation in the infrared range.

The thickness of the second layer 21 is also of the order of the wavelength used for the detector. It is therefore, for example, between 0.1 and 1.5 µm.

FIGS. 4c and 4d illustrate the step (c) of production of a waveguide.

First, FIG. 4c illustrates a step of structuring the second layer 21 by photolithography and selective etching.

This structuring step makes it possible to obtain a pattern 210 corresponding to the waveguide.

In this same step, a demultiplexer of the waveguide, intended to generate a number n of light beams each having intensity I/n, where I is the light intensity injected by the laser source into the waveguide, or a coupler intended to ensure the coupling between the waveguide and the laser source which will subsequently be produced on the substrate, may also be produced.

FIG. 4d illustrates a step of structuring a third layer of material previously deposited on the pattern 210.

This third layer is produced from a material having a third optical index $n_3$, $n_3$ being less than $n_2$.

The material used to produce the third layer is typically $SiO_2$.

The pattern obtained has the reference 220.

The structure obtained makes it possible to define the waveguide 13.

FIG. 4e illustrates the step (d) of producing a photodetector 14. Of course, a plurality of photodetectors could be produced in this step.

When the photodetector is a photodiode, the way in which it is obtained depends on the mode of operation of the detector.

When it comprises a laser source generating light radiation in the visible range, the photodiode is produced directly on the substrate 10, when the latter is produced from Si. In the case in which the substrate is sapphire, for example, a semiconductor structure is bonded onto the substrate 10.

When the laser source emits light radiation in the infrared range, the photodetector is obtained by growth of an epitaxial Ge layer, directly starting from the layer 21 of the SOI stack, for example, or by molecular bonding of a composite semiconductor structure, for example GaAs, onto the layer 20 of $SiO_2$ (FIG. 4e).

In this regard, reference may be made to the article "*Ultrahigh speed germanium-on-silicon-on-insulator photodetectors for 1.31 and 1.55 μm operation*" by M. Rouvière et al. (Applied Physics Letters 87, 231109-2005).

The subsequent steps (e) and (f) consist in producing a laser source 12 on the first layer 20, then in producing the electrical interconnections between the various elements produced on the substrate 10.

FIG. 4f illustrates the final step (g) of the method consisting in producing the cavity 11 inside the substrate 10.

The cavity 11 may, for example, be produced by anisotropic etching of the silicon constituting the substrate 10, from the face 101 of the substrate to the face 100. This makes it possible to obtain a funnel shape for the cavity 11.

The cavity may also be obtained by deep reactive etching of the substrate 10, whether it consists of Si or another material.

The particle detector obtained in this way corresponds to the one illustrated in FIG. 1.

The method shows that it is easier to carry out all the operations on the same face 100 of the substrate 10, but without this implying limitation.

Figure 2:
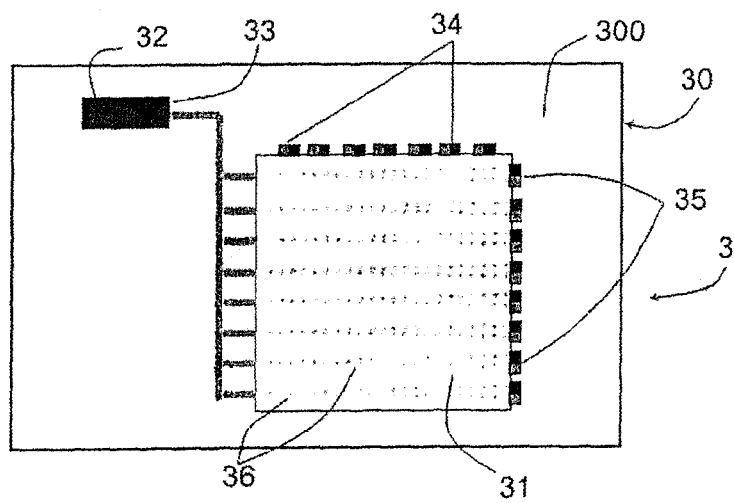
FIG. 2 is a plan view of a second exemplary embodiment of a particle detector according to the invention.
Figure 3:
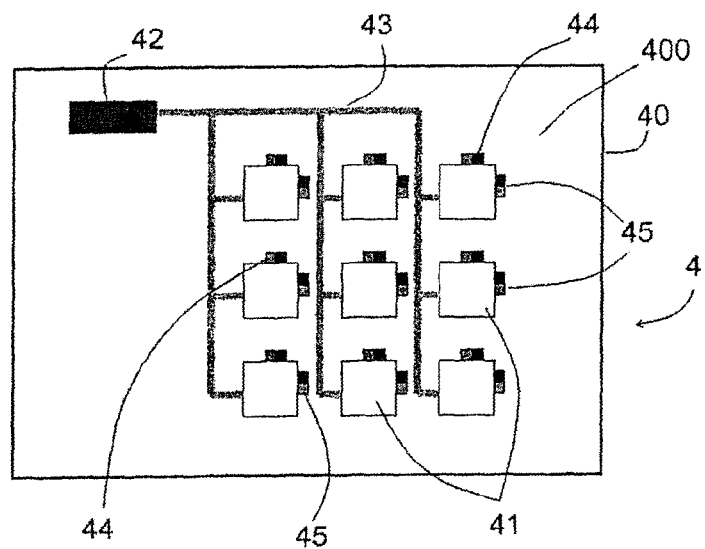
FIG. 3 is a plan view of a third exemplary embodiment of a particle detector according to the invention.

Reference will now be made to FIGS. 2 and 3, which illustrate two other exemplary embodiments of a particle detector according to the invention.

On a face 300 of a substrate 30, the detector 3 illustrated in FIG. 2 comprises at least one laser source 32 and one waveguide 33, which is arranged so as to emit a plurality of light beams in proximity to the cavity 11.

In the example illustrated in FIG. 2, the waveguide 33 makes it possible to generate seven light beams 36, all of which are in the same plane, which coincides with that of the substrate.

Such a waveguide makes it possible to emit a plurality of independent light beams from a single laser source, these light beams being substantially equivalent in terms of quality and intensity. This may, in particular, be achieved by virtue of a demultiplexer. All these beams are emitted from the same edge of the cavity.

The detector 3 also comprises a plurality of photodetectors 34, which are placed in proximity to the cavity 31 while being offset with respect to the axis of the laser beams emitted by the waveguide 33. All the photodetectors are positioned along the same edge of the cavity.

In this exemplary embodiment, it also comprises a plurality of photodiodes 35 substantially facing the ends of the waveguide and separated therefrom by the cavity 31. All these photodiodes are located on the same edge of the cavity opposite the one where the ends of the waveguide emerge.

In the example illustrated in FIG. 2, the number of beams emitted by the waveguide is the same as the number of photodetectors (seven). This, however, is not essential. If the number of photodetectors is greater, the information collected about the particles will be larger. If the number of beams is greater, the number of errors will be reduced.

A detector of this type makes it possible to produce a grid or mapping of the space in which the particles and the light beams interact, by virtue of the use of a plurality of beams and a plurality of detectors in parallel.

Thus, each photodetector picks up a fraction of light which depends on the number of particles in the detection volume, their size, their position and the position of the photodetector. Analysis of the data coming from the photodetectors, according to the scatterometry technique, makes it possible to reconstruct the shape and position of the particles present in the volume.

This grid makes it possible to increase the discrimination capacity of the detector and also to be able to detect the particles in a fairly wide size range.

It may be noted that the device 3 may also comprise a plurality of laser sources which can generate light radiations at different wavelengths.

The detector then comprises a plurality of waveguides, each of them being connected to each of the laser sources, each associated with a demultiplexer. This embodiment makes it possible to obtain more information for a given particle size.

FIG. 3 illustrates another example of a detector according to the invention.

The latter comprises a plurality of cavities 41 formed in a substrate 40.

A waveguide 43 makes it possible to connect a light source 42 to each of the cavities 41 and therefore to emit a light beam into each of these cavities. The waveguide and the laser source are located on the same face 400 of the substrate.

Here again, known methods make it possible to produce the waveguide in such a way that the light beams emitted into each of the cavities 41 have a substantially identical quality and intensity.

For the waveguides illustrated in FIGS. 2 and 3, reference may in particular be made to the article "*Silicon-on insulator (SOI) phased-array wavelength multi/demultiplexer with extremely low polarization sensitivity*" by P. D. Trinh et al. (IEEE Photonics Technology Letters, vol. 9 No. 7, July 1997).

Associated with each of the cavities 41, there is a photodetector 44 which is offset with respect to the axis of the light beam emitted by the waveguide and a photodiode 45 located facing the end of the waveguide and separated therefrom by the cavity 41.

The detector 4 has the advantage of comprising a plurality of spaces of interaction between a flow of particles to be detected and a light beam.

It can therefore detect a large density of particles by virtue of prior distribution of the air flow between the various cavities 41, which makes it possible to generate a plurality of interaction volumes.

Furthermore, the detector 4 makes it possible to reduce the risks of underestimating the number of particles.

This is because the probability that two particles will be present in the same cavity is proportional to the corresponding surface area made free in the substrate. It is therefore much lower in a detector comprising a plurality of cavities with smaller dimensions than in a single detector having a cross section comparable to the sum of the cross sections of the smaller cavities.

In the example illustrated, the cavities 41 have a square cross section and the length of a side of the square will typically be between 10 and 100 microns, while the dimension of the particles to be detected is between 1 and 10 microns.

Lastly, by virtue of a plurality of cavities of smaller size being placed in parallel, the detector 4 has the same effectiveness as a detector having a single cavity with a larger size.

Of course, the invention is not limited to the embodiments of the detector which have just been described.

The invention claimed is:

1. A particle detector for detecting particles in the ambient air, the particle detector comprising:
a substrate in which at least one through-cavity, delimited by an entry cross section and an exit cross section, is formed, the entry cross section being further configured to be connected to a source of an air flow, said air flow comprising the particles to be detected and capable of being received and directed by the said at least one through-cavity, said substrate supporting:
an optical device comprising at least one laser source and at least one waveguide, which is connected to said at least one laser source and the end of which is located in proximity to the exit cross section of said cavity, and
at least one photodetector located in proximity to the exit cross section of said cavity and offset with respect to the optical axis of said optical means, in order to detect the scattered light,
wherein the optical device and the photodetector are located on the same face of the substrate, the optical device and the photodetector being produced simultaneously on the same substrate or being integral with the substrate.

2. The particle detector as claimed in claim 1, wherein said at least one cavity has a variable cross section which decreases from the entry cross section to the exit cross section.

3. The particle detector as claimed in claim 1, wherein the optical device includes at least one photonic device, at the opposite end of the waveguide from the laser source.

4. The particle detector as claimed in claim 1, wherein the particle detector comprises a plurality of photodetectors associated with the through-cavity.

5. The particle detector as claimed in claim 1, wherein the substrate comprises a plurality of through-cavities.

6. The particle detector as claimed in claim 1, wherein the substrate comprises a semiconductor material.

7. The particle detector as claimed in claim 1, wherein the photodetector is a photodiode.

8. The particle detector as claimed in claim 1, wherein the opposite end of the waveguide from the laser source is nanostructured so as to produce a focusing function.

9. The particle detector as claimed in claim 1, wherein the substrate comprises silicon.

10. The particle detector as claimed in claim 1, wherein the waveguide comprises:
a first structure layer of a material having a first optical index n1,
a second layer of a material having a second optical index n2 on this first layer, n2 being greater than n1, and
a third structured layer of a material having a third optical index n3, wherein n3 is less than n2.

11. The particle detector as in claim 10, wherein the photodetector is offset with respect to the optical axis.

12. The particle detector as claimed in claim 1, wherein the through-cavity is formed on a surface of the substrate via etching.

13. The particle detector as claimed in claim 1, wherein the optical device and the photodetector are formed on a same face of the substrate.

14. The particle detector as claimed in claim 1, wherein the photodetector is selected from the group consisting of a pyrometer, bolometer, and photodiode.

15. The particle detector as claimed in claim 1, wherein the waveguide is configured to generate at least 7 light beams that are in the same plane and coincide with a plane of the substrate.

16. The particle detector as claimed in claim 1, wherein the laser source is configured to emit light in the infrared range, and wherein the photodetector includes an epitaxial germanium layer overlying a layer of silicon oxide.

17. The particle detector as claimed in claim 1, wherein the through-cavity has a funnel shape.

18. The particle detector as claimed in claim 1, wherein the particle detector comprises a plurality of photodetectors that are each associated with a plurality of said through cavities, and wherein said waveguide is configured to direct a light beam to each of said through cavities, said light beam being emitted from a single laser source.

19. The particle detector as claimed in claim 18, wherein each photodetector is offset with respect to the axis of the light beam emitted from the laser source, and are positioned facing the end of the waveguide and separated therefrom by each corresponding through cavity.

20. The particle detector as claimed in claim 1, wherein the particle detector is an optical particle counter.

* * * * *